US006996475B2

(12) United States Patent
Balaban (10) Patent No.: US 6,996,475 B2
(45) Date of Patent: *Feb. 7, 2006

(54) COMPUTER SOFTWARE PRODUCTS FOR NUCLEIC ACID HYBRIDIZATION ANALYSIS

(75) Inventor: David Balaban, San Jose, CA (US)

(73) Assignee: Affymatrix, Inc, Santa Clara, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 10/315,919

(22) Filed: Dec. 9, 2002

(65) Prior Publication Data

US 2004/0002817 A1 Jan. 1, 2004

Related U.S. Application Data

(63) Continuation of application No. 09/745,272, filed on Dec. 20, 2000, now Pat. No. 6,510,391.

(60) Provisional application No. 60/252,808, filed on Nov. 22, 2000.

(51) Int. Cl.
G06F 19/00 (2006.01)
C12Q 1/68 (2006.01)
G11C 17/00 (2006.01)
(52) U.S. Cl. .............................. 702/19; 435/6; 365/94
(58) Field of Classification Search ................ 702/19; 435/6; 365/94
See application file for complete search history.

(56) References Cited

U.S. PATENT DOCUMENTS 6,420,108 B2  7/2002  Mack et al.

OTHER PUBLICATIONS

Li et al, Model-based analysis of oligonucleotide arrays: Expression index computation and outlier detection, Jan. 2001, PNAS, vol. 98, No. 1, pp. 31-36.
Steven R. Gullans (2000), "Of Microarrays and Meandering Data Points", Nature Genetics, vol. 26, No. 1, pp. 4-5, http://www.nature.com, Aug. 26, 2002.
Stefanie Fuhrman, et al., "The Application of Shannon Entropy in the Identification of Putative Drug Targets", BioSystems 55 (2000), Neurobiology Department, Incyte Pharaceuticals Inc., 3174 Porter Drive, Palo Alto, CA 94304, USA, pps. 5-14.
George C. Tseng, et al., "Issues in cDNA Microarray Analysis: Quality Filtering, Channel Normalization, Models of Variations and Assessment of Gene Effects", Nucleic Acids Research 2001, vol. 29, No. 12, 2549-2557, © 2001 Oxford University Press.
Johannes Schuchardt, et al., "Normalization Strategies for cDNAS Microarrays", Nucleic Acids Research, 2000, vol. 28, No. 10 E47-e47, © 2000 Oxford University Press.

Primary Examiner—John S. Brusca
(74) Attorney, Agent, or Firm—Philip L. McGarrigle; Wei Zhou (57) ABSTRACT

Methods and computer software products are provided for analyzing gene expression data. In one embodiment, multiple probes are used to detect a single transcript. The hybridization intensities of each probe is adjusted by dividing the intensities by the affinities of the probes. The minimal adjusted hybridization intensity may be used as the measurement of the gene expression.

5 Claims, 3 Drawing Sheets

COMPUTER SOFTWARE PRODUCTS FOR NUCLEIC ACID HYBRIDIZATION ANALYSIS

RELATED APPLICATIONS

This application is a continuation of U.S. patent application Ser. No. 09/745,272, filed on Dec. 20, 2000, U.S. Pat. No. 6,510,391. U.S. Patent Application claims priority on U.S. Provisional Patent Application No. 60/252,808, filed on Nov. 22, 2000. These applications are incorporated herein by reference for all purposes.

FIELD OF INVENTION

This invention is related to bioinformatics and biological data analysis. Specifically, this invention provides methods, computer software products and systems for the analysis of biological data.

BACKGROUND OF THE INVENTION

Many biological functions are carried out by regulating the expression levels of various genes, either through changes in the copy number of the genetic DNA, through changes in levels of transcription (e.g. through control of initiation, provision of RNA precursors, RNA processing, etc.) of particular genes, or through changes in protein synthesis. For example, control of the cell cycle and cell differentiation, as well as diseases, are characterized by the variations in the transcription levels of a group of genes.

Recently, massive parallel gene expression monitoring methods have been developed to monitor the expression of a large number of genes using nucleic acid array technology which was described in detail in, for example, U.S. Pat. No. 5,871,928; de Saizieu, et al., 1998, *Bacteria Transcript Imaging by Hybridization of total RNA to Oligonucleotide Arrays*, NATURE BIOTECHNOLOGY, 16:45–48; Wodicka et al., 1997, *Genome-wide Expression Monitoring in Saccharomyces cerevisiae*, NATURE BIOTECHNOLOGY 15:1359–1367; Lockhart et al., 1996, *Expression Monitoring by Hybridization to High Density Oligonucleotide Arrays*. NATURE BIOTECHNOLOGY 14:1675–1680; Lander, 1999, *Array of Hope*, NATURE-GENETICS, 21(suppl.), at 3.

Massive parallel gene expression monitoring experiments generate unprecedented amounts of information. For example, a commercially available GeneChip® array set is capable of monitoring the expression levels of approximately 6,500 murine genes and expressed sequence tags (ESTs) (Affymetrix, Inc, Santa Clara, Calif., USA). Array sets for approximately 60,000 human genes and EST clusters, 24,000 rat transcripts and EST clusters and arrays for other organisms are also available from Affymetrix. Effective analysis of the large amount of data may lead to the development of new drugs and new diagnostic tools. Therefore, there is a great demand in the art for methods for organizing, accessing and analyzing the vast amount of information collected using massive parallel gene expression monitoring methods.

SUMMARY OF THE INVENTION

The current invention provides methods, systems and computer software products suitable for analyzing data from gene expression monitoring experiments that employ multiple probes against a single target.

Computer implemented methods for determining hybridization between a plurality of nucleic acid probes and a nucleic acid target are provided. The methods are useful for analyzing any hybridization between multiple probes and a target nucleic acid. It is particularly useful for analyzing gene expression experiments where a single transcript is determined using multiple probes.

In some embodiments, the method include steps of inputting a plurality of hybridization intensities, each of the intensities reflects the hybridization between one of the plurality of the probes and the nucleic acid target; adjusting the hybridization intensities for hybridization affinities of the probes to obtain a plurality of adjusted hybridization intensities; finding the minimal adjusted hybridization intensity among the adjusted hybridization intensities; and indicating the minimal adjusted hybridization intensity as a measurement of the hybridization. The hybridization affinities of the probes may be predicted based upon the sequence of the probes. The hybridization affinities may be inputted from a database where experimentally determined hybridization affinities are stored. The adjusted hybridization intensity are calculated according to:

$$\text{Adjusted hybridization intensity} = \frac{I}{\Gamma};$$

where I is hybridization intensity and $\Gamma$ is hybridization affinity.

In another aspect of the invention, computer software products are provided for determining hybridization between nucleic acid probes and a nucleic acid target. A software product may include a computer-readable medium having computer-executable instructions for performing the method of the invention.

In some embodiments, the software products may include computer program code for inputting a plurality of hybridization intensities, each of the hybridization intensities reflects the hybridization between one of the plurality of the probes and the nucleic acid target; computer program code for adjusting the hybridization intensities for hybridization affinities of the probes to obtain a plurality of adjusted hybridization intensities; computer program code for finding the minimal adjusted hybridization intensity among the adjusted hybridization intensities; and computer program code for indicating the minimal adjusted hybridization intensity as a measurement of said hybridization; and a computer readable media for storing the code.

The hybridization affinities of the probes may be predicted based upon the sequence of said probes and the software products contain code for performing the prediction. Alternatively, the predicted hybridization affinities may be inputted. In some embodiments, the hybridization affinities are inputted from a database. Hybridization affinities may also be measured experimentally. In preferred embodiments, the adjusted hybridization intensity may be calculated according to:

$$\text{Adjusted hybridization intensity} = \frac{I}{\Gamma},$$

where I is hybridization intensity and said $\Gamma$ is the hybridization affinity.

In yet another aspect of the invention, systems for analyzing nucleic acid hybridization are provided. In some embodiments, the system may include a processor; and a memory being coupled to the processor, the memory storing a plurality machine instructions that cause the processor to perform the method of the invention.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE PREFERRED EMBODIMENTS

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention. All cited references, including patent and non-patent literature, are incorporated herein by reference in their entireties for all purposes.

I. Gene Expression Monitoring with High Density Oligonucleotide Probe Arrays

High density nucleic acid probe arrays, also referred to as "DNA Microarrays," have become a method of choice for monitoring the expression of a large number of genes. As used herein, "Nucleic acids" may include any polymer or oligomer of nucleosides or nucleotides (polynucleotides or oligonucleotidies), which include pyrimidine and purine bases, preferably cytosine, thymine, and uracil, and adenine and guanine, respectively. See Albert L. Lehninger, PRINCIPLES OF BIOCHEMISTRY, at 793–800 (Worth Pub. 1982) and L. Stryer BIOCHEMISTRY, $4^{th}$ Ed., (March 1995), both incorporated by reference. "Nucleic acids" may include any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

"A target molecule" refers to a biological molecule of interest. The biological molecule of interest can be a ligand, receptor, peptide, nucleic acid (oligonucleotide or polynucleotide of RNA or DNA), or any other of the biological molecules listed in U.S. Pat. No. 5,445,934 at col. 5, line 66 to col. 7, line 51. For example, if transcripts of genes are the interest of an experiment, the target molecules would be the transcripts. Other examples include protein fragments, small molecules, etc. "Target nucleic acid" refers to a nucleic acid (often derived from a biological sample) of interest. Frequently, a target molecule is detected using one or more probes. As used herein, a "probe" is a molecule for detecting a target molecule. It can be any of the molecules in the same classes as the target referred to above. A probe may refer to a nucleic acid, such as an oligonucleotide, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that there are illustrative embodiments that are not to limit the invention in any way.

In preferred embodiments, probes may be immobilized on substrates to create an array. An "array" may comprise a solid support with peptide or nucleic acid or other molecular probes attached to the support. Arrays typically comprise a plurality of different nucleic acids or peptide probes that are coupled to a surface of a substrate in different, known locations. These arrays, also described as "microarrays" or colloquially "chips" have been generally described in the art, for example, in Fodor et al., Science, 251:767–777 (1991), which is incorporated by reference for all purposes. Methods of forming high density arrays of oligonucleotides, peptides and other polymer sequences with a minimal number of synthetic steps are disclosed in, for example, U.S. Pat. Nos. 5,143,854, 5,252,743, 5,384,261, 5,405,783, 5,424,186, 5,429,807, 5,445,943, 5,510,270, 5,677,195, 5,571,639, 6,040,138, all incorporated herein by reference for all purposes. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668, U.S. Pat. Nos. 5,677,195, 5,800,992 and 6,156,501 which disclose methods of forming vast arrays of peptides, oligonucleotides and other molecules using, for example, light-directed synthesis techniques. See also, Fodor et al., Science, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. Pat. Nos. 5,384,261 and 5,677,195.

Methods for making and using molecular probe arrays, particularly nucleic acid probe arrays are also disclosed in, for example, U.S. Pat. Nos. 5,143,854, 5,242,974, 5,252, 743, 5,324,633, 5,384,261, 5,405,783, 5,409,810, 5,412,087, 5,424,186, 5,429,807, 5,445,934, 5,451,683, 5,482,867, 5,489,678, 5,491,074, 5,510,270, 5,527,681, 5,527,681, 5,541,061, 5,550,215, 5,554,501, 5,556,752, 5,556,961, 5,571,639, 5,583,211, 5,593,839, 5,599,695, 5,607,832, 5,624,711, 5,677,195, 5,744,101, 5,744,305, 5,753,788, 5,770,456, 5,770,722, 5,831,070, 5,856,101, 5,885,837, 5,889,165, 5,919,523, 5,922,591, 5,925,517, 5,658,734, 6,022,963, 6,150,147, 6,147,205, 6,153,743, 6,140,044 and D430024, all of which are incorporated by reference in their entireties for all purposes. Typically, a nucleic acid sample is a labeled with a signal moiety, such as a fluorescent label. The sample is hybridized with the array under appropriate conditions. The arrays are washed or otherwise processed to remove non-hybridized sample nucleic acids. The hybridization is then evaluated by detecting the distribution of the label on the chip. The distribution of label may be detected by scanning the arrays to determine florescence intensities distribution. Typically, the hybridization of each probe is reflected by several pixel intensities. The raw intensity data may be stored in a gray scale pixel intensity file. The GATC™ Consortium has specified several file formats for storing array intensity data. The final software specification is available at www.gateconsortium.org and is incorporated herein by reference in its entirety. The pixel intensity files are usually large. For example, a GATC™ compatible image file may be approximately 50 Mb if there are about 5000 pixels on each of the horizontal and vertical axes and if a two byte integer is used for every pixel intensity. The pixels may be grouped into cells (see, GATC™ software specification). The probes in a cell are designed to have the same sequence (i.e., each cell is a probe area). A CEL file contains the statistics of a cell, e.g., the 75 percentile and standard deviation of intensities of pixels in a cell. The 50, 60, 65, 70, 80, 85 percentile of pixel intensity of a cell is often used as the intensity of the cell. Methods for signal detection and processing of intensity data are additionally disclosed in, for example, U.S. Pat. Nos. 5,547,839, 5,578,832, 5,631,734, 5,800,992, 5,856,092, 5,936,324, 5,981,956, 6,025,601, 6,090,555, 6,141,096, 6,141,096, and 5,902,723. Methods for array based assays, computer software for data analysis and applications are additionally disclosed in, e.g., U.S. Pat. Nos. 5,527,670, 5,527,676, 5,545,531, 5,622,829, 5,631, 128, 5,639,423, 5,646,039, 5,650,268, 5,654,155, 5,674,742, 5,710,000, 5,733,729, 5,795,716, 5,814,450, 5,821,328, 5,824,477, 5,834,252, 5,834,758, 5,837,832, 5,843,655, 5,856,086, 5,856,104, 5,856,174, 5,858,659, 5,861,242, 5,869,244, 5,871,928, 5,874,219, 5,902,723, 5,925,525, 5,928,905, 5,935,793, 5,945,334, 5,959,098, 5,968,730, 5,968,740, 5,974,164, 5,981,174, 5,981,185, 5,985,651, 6,013,440, 6,013,449, 6,020,135, 6,027,880, 6,027,894, 6,033,850, 6,033,860, 6,037,124, 6,040,138, 6,040,193, 6,043,080, 6,045,996, 6,050,719, 6,066,454, 6,083,697, 6,114,116, 6,114,122, 6,121,048, 6,124,102, 6,130,046, 6,132,580, 6,132,996, 6,136,269 and Ser. Nos. 08/736,743 and 09/737,536 all of which are incorporated by reference in their entireties for all purposes.

Nucleic acid probe array technology, use of such arrays, analysis array based experiments, associated computer software, composition for making the array and practical applications of the nucleic acid arrays are also disclosed, for example, in the following U.S. patent application Ser. Nos.: 07/838,607, 07/883,327, 07/978,940, 08/030,138, 08/082, 937, 08/143,312, 08/327,522, 08/376,963, 08/440,742, 08/533,582, 08/643,822, 08/772,376, 09/013,596, 09/016, 564, 09/019,882, 09/020,743, 09/030,028, 09/045,547, 09/060,922, 09/063,311, 09/076,575, 09/079,324, 09/086, 285, 09/093,947, 09/097,675, 09/102,167, 09/102,986, 09/122,167, 09/122,169, 09/122,216, 09/122,304, 09/122, 434, 09/126,645, 09/127,115, 09/132,368, 09/134,758, 09/138,958, 09/146,969, 09/148,210, 09/148,813, 09/170, 847, 09/172,190, 09/174,364, 09/199,655, 09/203,677, 09/256,361, 09/285,658, 09/294,293, 09/318,775, 09/326, 137, 09/326,374, 09/341,302, 09/354,935, 09/358,664, 09/373,984, 09/377,907, 09/383,986, 09/394,230, 09/396, 196, 09/418,044, 09/418,946, 09/420,805, 09/428,350, 09/431,964, 09/445,734, 09/464,350, 09/475,209, 09/502, 048, 09/510,643, 09/513,300, 09/516,388, 09/528,414, 09/535,142, 09/544,627, 09/620,780, 09/640,962, 09/641, 081, 09/670,510, 09/685,011, and 09/693,204 and in the following Patent Cooperative Treaty (PCT) applications/ publications: PCT/NL90/00081, PCT/GB91/00066, PCT/ US91/08693, PCT/US91/09226, PCT/US91/09217, WO/93/ 10161, PCT/US92/10183, PCT/GB93/00147, PCT/US93/ 01152, WO/93/22680, PCT/US93/04145, PCT/US93/ 08015, PCT/US94/07106, PCT/US94/12305, PCT/GB95/ 00542, PCT/US95/07377, PCT/US95/02024, PCT/US96/ 05480, PCT/US96/11147, PCT/US96/14839, PCT/US96/ 15606, PCT/US97/01603, PCT/US97/02102, PCT/GB97/ 005566, PCT/US97/06535, PCT/GB97/01148, PCT/GB97/ 01258, PCT/US97/08319, PCT/US97/08446, PCT/US97/ 10365, PCT/US97/17002, PCT/US97/16738, PCT/US97/ 19665, PCT/US97/20313, PCT/US97/21209, PCT/US97/ 21782, PCT/US97/23360, PCT/US98/06414, PCT/US98/ 01206, PCT/GB98/00975, PCT/US98/04280, PCT/US98/ 04571, PCT/US98/05438, PCT/US98/05451, PCT/US98/ 12442, PCT/US98/12779, PCT/US98/12930, PCT/US98/ 13949, PCT/US98/15151, PCT/US98/15469, PCT/US98/ 15458, PCT/US98/15456, PCT/US98/16971, PCT/US98/ 16686, PCT/US99/19069, PCT/US98/18873, PCT/US98/ 18541, PCT/US98/19325, PCT/US98/22966, PCT/US98/ 26925, PCT/US98/27405 and PCT/IEB99/00048, all of which are incorporated by reference in their entireties for all purposes. All the above cited patent applications and other references cited throughout this specification are incorporated herein by reference in their entireties for all purposes.

The embodiments of the invention will be described using GeneChip® high oligonucleotide density probe arrays (available from Affymetrix, Inc., Santa Clara, Calif., USA) as exemplary embodiments. One of skill the art would appreciate that the embodiments of the invention are not limited to high density oligonucleotide probe arrays. In contrast, the embodiments of the invention are useful for analyzing any parallel large scale biological analysis, such as those using nucleic acid probe array, protein arrays, etc.

Gene expression monitoring using GeneChip® high density oligonucleotide probe arrays are described in, for example, Lockhart et al., 1996, Expression Monitoring By Hybridization to High Density Oligonucleotide Arrays, Nature Biotechnology 14:1675–1680; U.S. Pat. Nos. 6,040, 138 and 5,800,992, all incorporated herein by reference in their entireties for all purposes.

In the preferred embodiment, oligonucleotide probes are synthesized directly on the surface of the array using photolithography and combinatorial chemistry as disclosed in several patents previous incorporated by reference. In such embodiments, a single square-shaped feature on an array contains one type of probe. Probes are selected to be specific against desired target. Methods for selecting probe sequences are disclosed in, for example, U.S. patent application Ser. No. 09/718,295, filed Nov. 21, 2000, U.S. patent application Ser. No. 09/721,042, filed Nov. 21, 2000, and U.S. patent application Ser. No. 60/252,617, filed Nov. 21, 2000, all incorporated herein by reference in their entireties for all purposes.

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20 mer sequence complementary to an IL-2 mRNA. There, however, may exist 20 mer subsequences that are not unique to the IL-2 mRNA. Probes directed to these subsequences are expected to cross hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

Probes as short as 15, 20, 25 or 30 nucleotides are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

In some preferred embodiments, the expression of a particular transcript may be detected by a plurality of probes, typically, up to 5, 10, 15, 20, 30 or 40 probes. Each of the probes may target different sub-regions of the transcript. However, probes may overlap over targeted regions.

In some preferred embodiments, each target sub-region is detected using two probes: a perfect match (PM) probe that is designed to be completely complementary to a reference or target sequence. In some other embodiments, a PM probe may be substantially complementary to the reference sequence. A mismatch (MM) probe is a probe that is designed to be complementary to a reference sequence except for some mismatches that may significantly affect the hybridization between the probe and its target sequence. In preferred embodiments, MM probes are designed to be complementary to a reference sequence except for a homomeric base mismatch at the central (e.g., $13^{th}$ in a 25 base probe) position. Mismatch probes are normally used as controls for cross-hybridization. A probe pair is usually composed of a PM and its corresponding MM probe. The difference between PM and MM provides an intensity difference in a probe pair.

II. Data Analysis Systems

In one aspect of the invention, methods, computer software products and systems are provided for computational analysis of microarray intensity data for determining the presence or absence of genes in a given biological sample. Accordingly, the present invention may take the form of data analysis systems, methods, analysis software, etc. Software written according to the present invention is to be stored in some form of computer readable medium, such as memory, or CD-ROM, or transmitted over a network, and executed by a processor. For a description of basic computer systems and computer networks, see, e.g., Introduction to Computing Systems: From Bits and Gates to C and Beyond by Yale N. Patt, Sanjay J. Patel, 1st edition (Jan. 15, 2000) McGraw Hill Text; ISBN: 0072376902; and Introduction to Client/Server Systems: A Practical Guide for Systems Professionals by Paul E. Renaud, 2nd edition (June 1996), John Wiley & Sons; ISBN: 0471133337.

Computer software products may be written in any of various suitable programming languages, such as C. C++. C# (Microsoft®), Fortran, Perl, MatLab (MathWorks, www-.mathworks.com), SAS, SPSS and Java. The computer software product may be an independent application with data input and data display modules. Alternatively, the computer software products may be classes that may be instantiated as distributed objects. The computer software products may also be component software such as Java Beans (Sun Microsystem), Enterprise Java Beans (EJB, Sun Microsystems), Microsoft® COM/DCOM (Microsoft®), etc.

Figure 1:
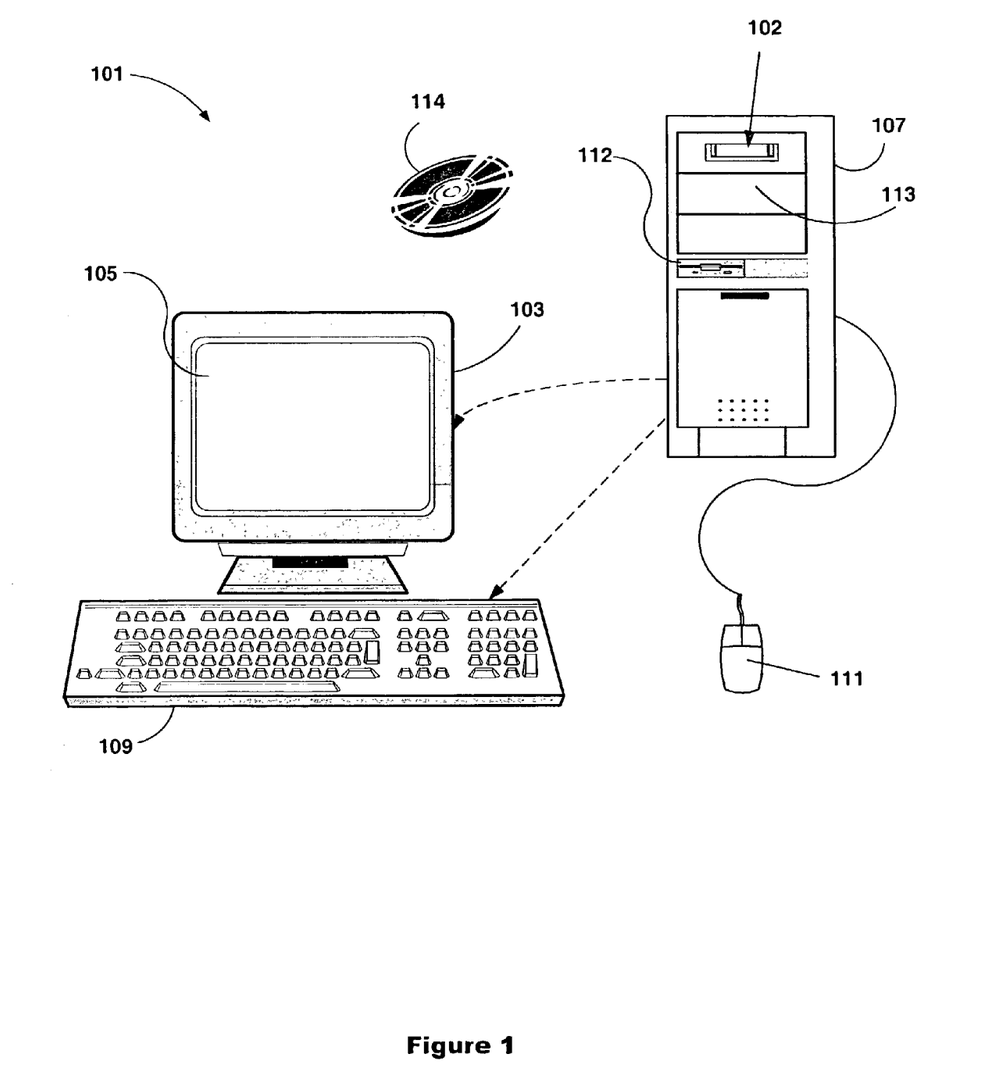
FIG. 1 illustrates an example of a computer system that may be utilized to execute the software of an embodiment of the invention.

FIG. 1 illustrates an example of a computer system that may be used to execute the software of an embodiment of the invention. The computer system described herein is also suitable for hosting a DBMS. FIG. 1 shows a computer system 101 that includes a display 103, screen 105, cabinet 107, keyboard 109, and mouse 111. Mouse 111 may have one or more buttons for interacting with a graphic user interface. Cabinet 107 houses a floppy drive 112, CD-ROM or DVD-ROM drive 102, system memory and a hard drive (113) (see also FIG. 2) which may be utilized to store and retrieve software programs incorporating computer code that implements the invention, data for use with the invention and the like. Although a CD 114 is shown as an exemplary computer readable medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
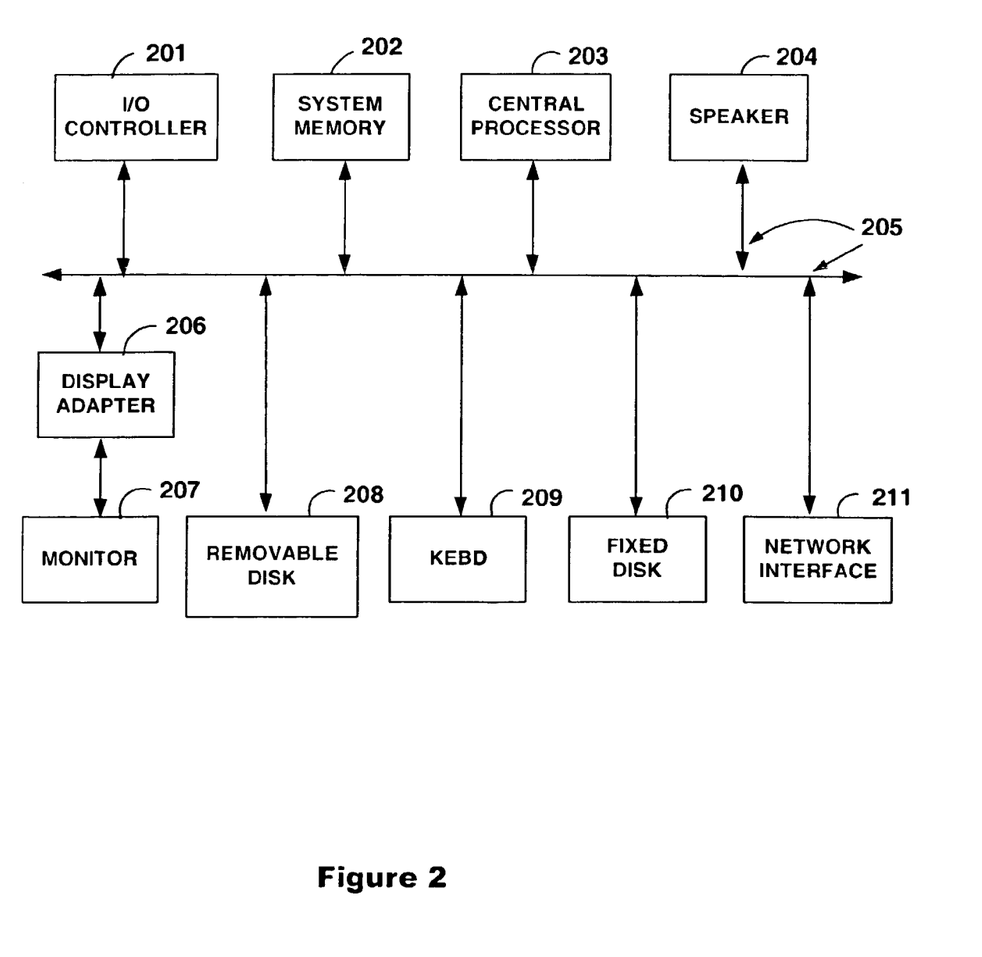
FIG. 2 illustrates a system block diagram of the computer system of FIG. 1.

FIG. 2 shows a system block diagram of computer system 101 used to execute the software of an embodiment of the invention. As in FIG. 1, computer system 101 includes monitor 201, and keyboard 209. Computer system 101 further includes subsystems such as a central processor 203 (such as a Pentium™ III processor from Intel), system memory 202, fixed storage 210 (e.g., hard drive), removable storage 208 (e.g., floppy or CD-ROM), display adapter 206, speakers 204, and network interface 211. Other computer systems suitable for use with the invention may include additional or fewer subsystems. For example, another computer system may include more than one processor 203 or a cache memory. Computer systems suitable for use with the invention may also be embedded in a measurement instrument.

III. Analysis of Hybridization of Probe Sets and Their Targets

The method of the invention will be explained in great detail using the above terminology associated with Affymetrix GeneChip® probe arrays. One of skill in the art would appreciate that the method of the invention is generally applicable to biological analysis using multiple probes (or other means of obtaining multiple measurements against one biological variable, such as level of a transcript, etc.).

A typical situation for current implementation and usage for the GeneChip® probe array expression analysis is that there are 10, 15 or 20 probe pairs for each gene and a group of experiments to be compared among each other. It is apparent to those skilled in the art, the current invention is not limited to the number of probe pairs. Preferably, the methods, systems and inventions are used to analyze data from experiments that employ at least two probe pairs, more preferably more than five probe pairs.

Some embodiments of the methods, systems and computer software products of the invention is based upon an algorithm for analyzing gene expression levels. The following notations are used to describe preferred embodiments. One of skill in the art would appreciate that the specific notations and mathematical equations are provided for the purpose of best describing the invention. The methods, systems and computer software products of the invention are not limited by the specific notations or equations.

In gene expression experiment, the target transcripts are denoted as:

$t_1, t_2, t_3 \ldots$

If multiple experiments are conducted, the experiments are denoted as:

$E_1, E_2, E_3 \ldots$

Nucleic acid probe arrays (Chips) are denoted as:

$A_1, A_2, A_3 \ldots$

Probes on a chip are denoted as $P_1, P_2, P_3 \ldots$ $X(P_j)$ is the x coordinate of the cell containing probe j $Y(P_j)$ is the y coordinate of the cell containing probe j T=The set of all transcripts potentially existing in the target solution for any experiment, $T=\{t_1, t_2, t_3 \ldots\}$ $E_i(t_j)$=Concentration of transcript $t_j$ in experiment $E_i$ X $(P_j)$=(this will be zero for many combinations)

$D(P_j)$=The transcript probe $p_j$; $D(P_j)=t_j$

A model is provided to relate the observed intensity for a particular probe (such as an oligonucleotide sequence) on a chip, to the hybridization of that oligonucleotide to transcripts in the target solution. The model explicitly describes the contribution of "perfect match" hybridization and cross hybridization to the measured intensity.

For each probe $P_j$:

$$\alpha I_j - \beta = \Gamma_j C_{D(Pj)} + \chi_{j,T-\{D(pj)\}} \tag{1}$$

where $C_{D(Pj)}$=The concentration of the transcript measured by $P_j$;

$C=E_i(D(pj)); C(E_i)$ $I_j$=The measured intensity; $I(E_i, A_i, P_j)$ $\alpha$=The spatial variation correction factor; $\alpha(X(p_j),Y(p_j), E_i, A_i)$ $\beta$ The uniform offset (background) correction; $\beta(E_i, A_i)$ $\Gamma_j$=The hybridization affinity for probe $p_j$; $\Gamma(p_j, D(p_j))$ $$\chi_{j,T-\{D(pj)\}} = \text{The cross hybridization affinity probe } p_j \; \chi_{j,T-\{D(pj)\}} = \sum_{tk \neq D(Pj)} E_i(t_k) * \delta(t_k, P_j)$$

where $\delta(t_k, p_j)$ is the affinity probe $p_j$ to transcript $t_k$

It may be helpful to look at equation (1) without all the subscripts.

$$\alpha I - \beta = \Gamma C + \chi \tag{2}$$

The left-hand side of equation (2) represents the measured intensity for probe $p_j$ after all uniform effects have been removed. These uniform effects do not depend on the sequence of the probe or on the sequences in the target solution. In other words, they are sequence independent effects that depend on the experiment and on the manufacturing characteristics of the chip. We will call the left-hand side of equation (1) the adjusted intensity.

The right hand side of equation (2) describes the effect of hybridization on the adjusted intensity. The first term states that the adjusted intensity is a linear function of the target solution concentration. Specifically it is a linear function of the transcript in the target solution that contains the probe sequence. The second term states that the adjusted intensity is also proportional to the cross hybridization. That is, to the hybridization of the probe to all other transcripts in the target solution.

Cross hybridization is not a uniform, sequence independent process. It is not eliminated when the adjusted intensity is computed. It is a complex and unknown process but it is not random and uniform. Correctly managing cross hybridization is the essential new concept in the new algorithms.

To further simplify the notation, the adjusted intensity is designated as I'. That is:

$$I' = \Gamma C + \chi \tag{3}$$

Some embodiments of the algorithm assume that it is possible to predict the value of $\Gamma$ (hybridization affinity for probes) based on the sequence of the probe. Methods for predicting $\Gamma$ (hybridization affinity for probes) are described in, for example U.S. patent application Ser. No. 09/718,295, filed Nov. 21, 2000 and U.S. patent application Ser. No. 09/721,042, filed Nov. 21, 2000, both incorporated herein by reference for all purposes In some embodiments, a physical model that is based on the thermodynamic properties of the sequence is used to predict the array-based hybridization intensities of the sequence. Hybridization propensities may be described by energetic parameters derived from the probe sequence, and variations in hybridization and chip manufacturing conditions will result in changes in these parameters that can be detected and corrected. The values of weight coefficients in the physical model may be determined by empirical data because these values are influenced by assay conditions, which include hybridization and target fragmentation, and probe synthesis conditions, which include choice of substrates, coupling efficiency, etc.

In one embodiment, a model experimental system is used to generate empirical data and a computational model is used to process these data to solve for the weight coefficients of the physical model. These solved weight coefficients are in turn placed back into the physical model, enabling it to predict the hybridization behaviors of new sequences.

The equation (3) is divided by the known quantity $\chi$ to get:

$$\frac{I'}{\Gamma} = C + \frac{\chi}{\Gamma}$$

Because cross hybridization is difficult to be completely eliminated, $\chi \geq 0$:

$$\frac{I_1}{\Gamma_1} \geq C \text{ and that } \frac{I_1}{\Gamma_1} = C \text{ only if } \chi = 0.$$

This means that if $$\frac{I_1}{\Gamma_1}, \frac{I_2}{\Gamma_2}, \frac{I_3}{\Gamma_3}, \ldots$$

is a collection of concentration estimates for a particular transcript, based on a collection of different probes for that transcript, then the best estimate for the concentration of that transcript is:

$$\min\left\{\frac{I_1}{\Gamma_1}, \frac{I_2}{\Gamma_2}, \frac{I_3}{\Gamma_3}, \ldots\right\}. \tag{4}$$

The probes corresponding to a transcript will all respond differently to cross hybridization, and that at least a few of them will have very little cross hybridization.

The minimization in equation (3) does not require any assumptions about the stochastic behavior of cross hybridization. This provides a great advantage since cross hybridization is not well modeled as a random process.

Figure 3:
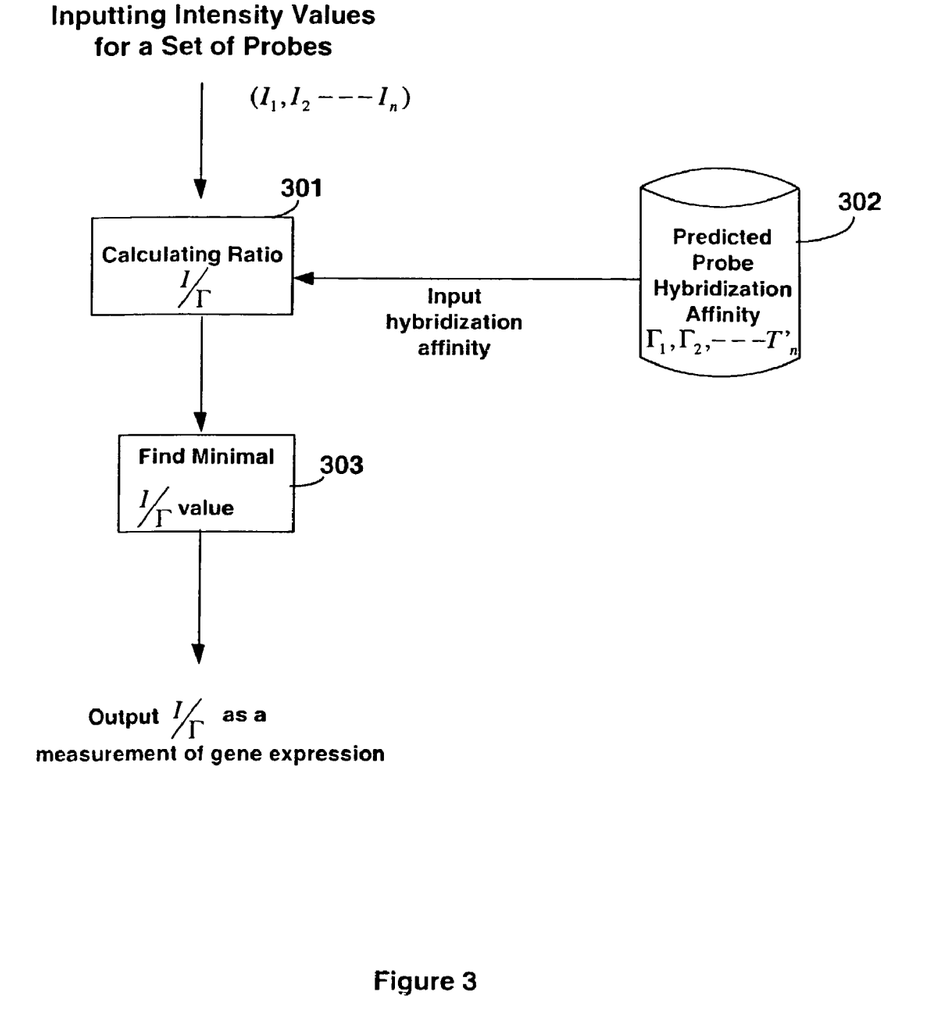
FIG. 3 shows one embodiment of the gene expression analysis method of the invention.

IV. Computer Implemented Methods, Computer Software and Systems for Multiple Probe Data Analysis In one aspect of the invention, computer implemented methods are used to analyze nucleic acid hybridization. The methods are particularly suitable for analyzing multiple probe array based gene expression analysis. FIG. 3 shows a process for some embodiments of the invention. Intensity values for a set of probes ($I_1, I_2 \ldots I_n$) are inputted (301). The probe set is designed to interrogate one transcript. In preferred embodiments, a probe set has at least 5, 10, 15 or 20 probes. The probes may be designed to be a perfect match with the target transcript. Alternatively, some of the probes may be designed as mismatch control. The intensity values may be the measured values for the prefect match probes. Alternatively, they may be the difference between the intensities for the perfect match probes and those of the mismatch probes. One of skill in the art would appreciate that the intensity values may be adjusted or normalized for background, non-specific bindings, etc.

The intensity values are adjusted using hybridization affinities of the probes. The predicted or measured hybridization affinity of the probes with their target may be pre-calculated and stored in a database (302). Hybridization affinity may be measured experimentally by hybridizing probes with their intended targets. In addition, hybridization affinity for probes may be predicted based upon the sequences of the probes. Methods, software products and systems for predicting hybridization affinity of probes are disclosed in, for example, U.S. paten applications Ser. No. 09/718,295, filed on Nov. 21, 2000, and Ser. No. 09/721,042 filed on Nov. 21, 2000, both incorporated herein by reference for all purposes.

One of skill in the art would appreciate that the methods, software products and systems are limited to any particular model and methods for predicting hybridization affinity of probes. Rather, the current invention may employ any suitable methods for predicting hybridization affinity. However, for illustration purposes, some preferred methods for predicting hybridization affinity are discussed below:

In this particular method, a physical model that is based on the thermodynamic properties of the sequence is used to predict the array-based hybridization intensities of the sequence. Hybridization propensities may be described by energetic parameters derived from the probe sequence, and variations in hybridization and chip manufacturing conditions will result in changes in these parameters that can be detected and corrected.

The values of weight coefficients in the physical model may be determined by empirical data because these values are influenced by assay conditions, which include hybridization and target fragmentation, and probe synthesis conditions, which include choice of substrates, coupling efficiency, etc.

Basically, a target (T) hybridizes to its complementary probe (P) to form a probe-target duplex (P·T), and the reaction is accompanied with favorable free energy change. The amplitude of the free energy change ($\Delta G$) determines the stability of probe-target duplex. The duplex stability can be described by equilibrium constant ($K_s$), which is sequence-dependent. The relationship between $K_s$ and $\Delta G$ may be given by Boltzmann's equation:

$$K_s = \frac{k_{on}}{k_{off}} = e^{-\Delta G/RT} \qquad (4)$$

where $k_{on}$ and $k_{off}$ are the rate constants for association and dissociation, respectively of the probe-target duplex, R is the gas constant and T is the absolute temperature. According to Equation 4, $\Delta G$ is a function of the sequence. The dependence of $\Delta G$ on probe sequence can be quite complicated, but relatively simple models for $\Delta G$ have yielded good results.

There are a number of ways to establish the relationship between the sequence and $\Delta G$. In preferred embodiments, Nathan Hunt's simple model (See, U.S. application Ser. No. 09/721,042, filed Nov. 21, 2000, previously incorporated by reference) works the best in some embodiments of the invention.

$$\Delta G_{seq} = \sum_{i=1}^{3N} P_i S_i \text{ or} \qquad (5)$$

$$\Delta G_{seq} = \sum_{i=1}^{3N} P_i S_i + C \qquad (6)$$

where N is the length (number of bases) of a probe. $P_i$ is the value of the ith parameter which reflects the $\Delta G$ of a base in a given sequence position relative to a reference base in the same position. In preferred embodiments, the reference base is A. In this case, the Pi's will be the free energy of a base in a given position relative to base A in the same position.

Based on the simple hybridization scheme described above, the hybridization intensity is proportional to the concentration of probe-target duplex, where $C_0$ is constant. Under equilibrium condition, the intensity is directly related to $\Delta G$. This relationship is also expressed in natural logarithm form, where $C_1$ and $C_2$ are constants. The relationship between intensity and probe sequence is described below:

$I=C_0[P \cdot T]$ $[P \cdot T]=K_s[P][T]=e^{-\Delta G/RT}[P][T]$ $LnI=-\Delta G/RT+Ln\{C_0[P][T]\}$ $$LnI = C_1 \sum_{i=1}^{3N} P_i S_i + C_2 \text{ or } LnI = \sum_{i=1}^{3N} C_1 P_i S_i + C_2 = \sum_{i=1}^{3N} W_i S_i + C_2$$

where $W_i = C_1 P_i$. The following is a linear regression model for probes of N bases in length using a training data set that contains intensity values of M probes.

$Ln(I_1)=W_1 S_{11}+W_2 S_{21}+\ldots W_{3N} S_{3N1}$ $Ln(I_2)=W_1 S_{12}+W_2 S_{22}+\ldots W_{3N} S_{3N2}$

.

.

.

$Ln(I_1)=W_1 S_{11}+W_2 S_{12}+\ldots W_{3N} S_{3N1}$

Hybridization intensities (relative to a reference base, such as an A) for each type of bases can be solved at each position in the probe sequence may be predicted. Multiple linear regression analysis is well known in the art, see, for example, electronic statistic book (statsoftinc.com/textbook/ stathome.html) Darlington, R. B. (1990). *Regression and linear models*. New York: McGraw-Hill, both incorporated by reference for all purposes. Computer software packages, such as SAS, SPSS, and MatLib 5.3 provide multiple linear regression functions. In addition, computer software code examples suitable for performing multiple linear regression analysis are provided in, for example, the Numerical Recipes (NR) books developed by Numerical Recipes Software and published by Cambridge University Press (CUP, with U.K. and U.S. web sites).

In a preferred embodiment, a set of probes of different sequences (probes 1 to M) is used as probes in experiments(s). Hybridization affinities (relative $\Delta G$ or $Ln (I)$) of the probes with their target are experimentally measured to obtain a training data set (see, example section infra). Multiple linear regression may be performed using hybridization affinities as I $[I_1 \ldots I_m]$ to obtain a set of weight coefficients: $[W_j \ldots W_N]$. The weight coefficients are then used to predict the hybridization affinities.

Continuing the process in FIG. 3, the predicted or measured probe hybridization affinity values may be stored in a database (302) or a file. Alternatively, hybridization affinities may be predicted as requested.

Adjusted hybridization intensity values may be calculated (301) as:

$$\frac{I}{\Gamma};$$

An adjusted hybridization intensity may be calculated for each probe (or probe pair if the intensity is the difference between a perfect match probe and a mismatch probe). In some other embodiments, the adjusted hybridization intensity may not be a simple ratio. One of skill in the art would appreciate that other methods for calculating the relative or adjusted hybridization intensities may also be used.

The minimal value of the adjusted intensity values (303) may be used as a measurement of gene expression.

Computer software products for gene expression analysis are also provided. The products may contain a computer readable medium containing code for performing the methods steps discussed above and in FIG. 3.

Computer systems for gene expression analysis are provided. The systems have a processor, a memory coupled to the processor, the memory storing machine instructions that cause the processor to perform a plurality of logical steps when implemented by the processor. The logic steps include the analysis steps discussed above.

Many embodiments of the invention are particularly useful for analyzing gene expression using nucleic acid probe arrays. As described above, such arrays contain a large number of sets of probes. Each set is used for measuring one transcript. In such embodiments, the process in FIG. 3 is repeated for each probe sets. It is generally preferable that all the probe sets (each is for measuring one transcript) in a probe array are analyzed using the methods, software or system of the invention. However, in some embodiments, a subset of the probe sets may be analyzed using the methods, systems and software of the invention.

CONCLUSION

The present inventions provide methods and computer software products for analyzing gene expression profiles. It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring transcript levels and gene expression monitoring at the protein level could be used. The scope of the invention should, therefore, be determined not with reference to the above description, but should instead be determined with reference to the appended claims, along with the full scope of equivalents to which such claims are entitled.

All cited references, including patent and non-patent literature, are incorporated herewith by reference in their entireties for all purposes.

What is claimed is:

1. A computer software product for determining hybridization between a plurality of nucleic acid probes and a nucleic acid target comprising:
    computer program code for inputting a plurality of hybridization intensities, each of said hybridization intensities reflects said hybridization between one of said plurality of said probes and said nucleic target;
    computer program code for adjusting said hybridization intensities for hybridization affinities of said probes to obtain a plurality of adjusted hybridization intensities;
    computer program code for finding the minimal adjusted hybridization intensity among said adjusted hybridization intensities; and
    computer program code for indicating said minimal adjusted hybridization intensity as a measurement of said hybridization; and
    wherein said computer program codes are stored in a computer readable media.

2. The computer software product of claim 1, wherein said hybridization affinities of said probes are predicted based upon the sequence of said probes.

3. The computer software product of claim 2, wherein said hybridization affinities are inputted from a database.

4. The computer software product of claim 3 wherein said hybridization affinities are measured experimentally.

5. The computer software product of claim 4 wherein said adjusted hybridization intensity are calculated according to:

$$\text{Adjusted hybridization intensity} = \frac{I}{\Gamma},$$

wherein said I is said hybridization intensity and said $\Gamma$ is said hybridization affinity.

* * * * *